US 6,668,185 B2

(12) United States Patent
Toida

(10) Patent No.: US 6,668,185 B2
(45) Date of Patent: Dec. 23, 2003

(54) ENDOSCOPE APPARATUS FOR SETTING A SCANNING AREA

(75) Inventor: Masahiro Toida, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 84 days.

(21) Appl. No.: 09/984,511

(22) Filed: Oct. 30, 2001

(65) Prior Publication Data

US 2002/0052547 A1 May 2, 2002

(30) Foreign Application Priority Data

Oct. 31, 2000 (JP) ........................................ 2000-332360
Oct. 18, 2001 (JP) ........................................ 2001-320408

(51) Int. Cl.⁷ .............................. A61B 6/00; A61B 8/00
(52) U.S. Cl. ....................... 600/425; 600/443; 600/117; 600/476; 356/450
(58) Field of Search ................................ 600/425, 473, 600/476, 478, 117, 160, 443; 356/450, 900; 128/916

(56) References Cited

U.S. PATENT DOCUMENTS 6,069,698 A * 5/2000 Ozawa et al. ............... 356/345
6,498,948 B1 * 12/2002 Ozawa et al. ............... 600/476
2002/0028010 A1 * 3/2002 Toida .......................... 382/131
2002/0051512 A1 * 5/2002 Toida .......................... 378/21
2002/0052547 A1 * 5/2002 Toida .......................... 600/425
2002/0198457 A1 * 12/2002 Tearney et al. ............. 600/476

FOREIGN PATENT DOCUMENTS

EP    1 201 182 A2 * 5/2002 ............ A61B/5/00

* cited by examiner

*Primary Examiner*—Shawna J Shaw
(74) *Attorney, Agent, or Firm*—Sughrue Mion, PLLC

(57) ABSTRACT

An endoscope apparatus that has an OCT function and can efficiently obtain an optical tomographic image is provided. An image of an area within a body cavity is displayed on a monitor, and an operator uses a pen-type input to specify a point thereon. An aiming-light is projected onto the body cavity and displayed on said monitor as a bright point, and a coated tube of an OCT probe is slid and rotated by a scanning controller so as to align the aiming-light with the point. A scanning-area setting means sets a ring shaped scanning area when the aiming-light and point are aligned. The scanning area is scanned with a signal-light, and an optical tomographic image is obtained and displayed on a monitor. An optical tomographic image can be efficiently and expediently obtained without the need to manually direct the irradiation position of the signal-light to a desired scanning area.

15 Claims, 6 Drawing Sheets

FIG.4
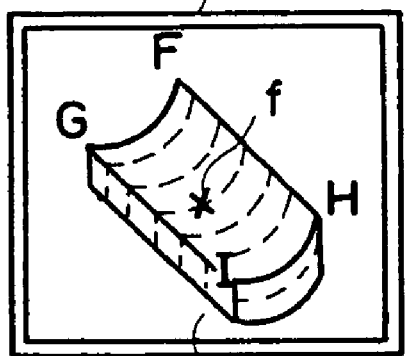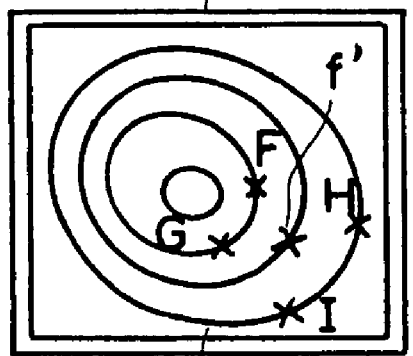

ENDOSCOPE APPARATUS FOR SETTING A SCANNING AREA

BACKGROUND OF THE INVENTION

1. Field of the Invention

The present invention relates in general to an endoscope apparatus, and in particular to an endoscope apparatus provided with a tomographic-image obtaining function for obtaining a tomographic image by scanning an examination area of a subject such as a human body with a signal-wave.

2. Description of the Related Art

There are in wide use in a variety of medical fields electron endoscope apparatuses for observing the interior of a body cavity of a patient, wherein an image formed of the light reflected from the interior of a body cavity of a patient upon the illumination thereof by an illuminating-light is obtained and displayed on a monitor or the like. Further, many endoscope apparatuses are provided with a forceps insertion port, and by inserting a probe therethrough into a body cavity of the patient, a biopsy on the tissue in the body cavity can be performed and treatment administered.

On the other hand, in recent years, efforts to develop a tomographic image obtaining apparatus for obtaining a tomographic image of a subject such as the human body have been advanced. Examples of known tomographic image obtaining apparatuses include: an optical tomographic image obtaining apparatus, which utilizes an optical interference caused by a low-coherence light; and an ultrasound tomographic image obtaining apparatus, which utilizes ultrasonic waves etc.

An OCT (Optical Coherence Tomography) apparatus, which obtains an optical tomographic image of an area of which a measurement is to be taken (hereinafter referred to simply as a measurement area) by measuring the intensity of an interference-light caused by a low-coherence light by heterodyne wave detection, is an example of an optical tomographic image obtaining apparatus; a detailed description thereof can be found in an article in "O Plus E" Vol. 21, No. 7, pp. 802–04, by Masamitsu Haruna.

According to the aforementioned OCT apparatus: the low-coherence light emitted from a light source formed of an SLD (Super Luminescent Diode) or the like, is separated into a signal-light and a reference-light; the frequency of the signal-light or the reference-light is slightly shifted by use of a Piezo element or the like; the measurement area is irradiated with the signal-light and interference is caused between the reference-light and the reflected-light reflected from a predetermined depth of said measurement portion; the signal strength of the interference signal produced due to said interference is measured by heterodyne wave detection; and the tomographic data is obtained; wherein, by very slightly moving a movable mirror or the like disposed above the optical path of the reference-light, causing the length of the optical path of the reference-light to change slightly, the length of the optical path of the reference-light and the length of the optical path of the signal-light can be made to be equal, and the data for a predetermined depth of the measurement portion can be obtained. Further, by moving the entry position of the signal-light in slight increments and repeating the measurement operation at each new point, the optical tomographic image of a predetermined scanning area can be obtained.

Because the early diagnosis of the depth of penetration of cancer or the like also becomes possible if an OCT apparatus such as that described above is utilized, efforts to develop methods of obtaining an optical tomographic image of the interior of a body cavity by guiding a signal-light and a reflected-light of the signal-light through an OCT probe that can be inserted into the forceps insertion port of the endoscope apparatus are being advanced. For example, according to an OCT apparatus described in an article in "Optics Letter", Vol. 24, No. 19, pp. 1358–60, by Andrew M Rollin and Rujchai Ung-arunyawee: an OCT probe provided with an optical fiber and a mirror, which is disposed at the distal end of this optical fiber, for reflecting the signal-light at a right angle is inserted through the forceps insertion port of the endoscope apparatus to the interior of a body cavity of a patient; radial scanning is carried out by rotating the mirror disposed at the distal end of the optical fiber; and a radial optical tomographic image, which is an optical tomographic image showing a wall of the interior of the body cavity in round cross-sections, is displayed.

Further, the same as for the OCT apparatus, efforts to develop a probe-shaped apparatus capable of being inserted into the forceps insertion port of an endoscope apparatus for use in conjunction with an ultrasonic tomographic image obtaining apparatus such as that described in "Ultrasound Examination and Diagnostic Techniques", Chapter 6, pp. 126–133 by Hiroaki Okawai, Toyo Press, and the like are being advanced, and the displaying of a tomographic image obtained by these apparatus, together with a reflectance image obtained by an endoscope, is in the process of being realized.

However, in order to employ the endoscope apparatus and probe for obtaining an optical tomographic image described above to obtain an optical tomographic image as described above, because it is necessary to first confirm by use of the endoscope the scanning area of which an optical tomographic image is to be obtained, and to manually guide the probe for obtaining an optical tomographic image to said scanning area. However, because this manual operation to guide the probe is troublesome, there is a problem in that the efficiency of the operation occurring when an optical tomographic image is to be obtained is reduced. Further, there is also a problem in that accurately positioning the distal end of the probe at a desired position is difficult.

SUMMARY OF THE INVENTION

The present invention has been developed in consideration of the circumstances described above, and it is a primary object of the present invention to provide an endoscope apparatus provided with an optical tomographic image obtaining function capable of efficiently obtaining an optical tomographic image of a desired scanning area.

The endoscope apparatus according the present invention comprises: a target-subject image obtaining means for projecting an illuminating-light onto the target subject, obtaining an image formed of the reflected-light reflected from the target subject upon the irradiation thereof with the illuminating-light, and forming a target-subject image based on said obtained image formed of said reflected-light; a target-subject image display means for displaying a target-subject image formed by said target-subject image obtaining means; and a tomographic image obtaining means for scanning a scanning area within the target subject with a signal-wave and obtaining a tomographic image of the scanned area; further comprising a position specifying means for specifying one or more desired points on a target-subject image displayed on the target-subject image display means, and a scanning-area setting means for setting a scanning area to be scanned with the signal-wave, based on the point(s) specified by the position specifying means.

Here, the referent of the term "illuminating-light" is not limited to white-light or other visible light, but also includes types of non-visible light such as infrared light and the like. Further, the expression "forming a target-subject image based on said obtained image formed of said reflected-light" can refer to forming a target-subject image by subjecting the image obtained by the image obtaining means to reflectance-image image processing, or forming a target-subject image by subjecting the image obtained by the image obtaining means to any of a number of specialized image-processing processes. As to the specialized image-processing processes, for cases in which the illuminating-light is anon-visible light such as infrared light, etc., an image processing process for converting the image obtained by the image obtaining means to a target-subject image formed of visible light, etc., can be used.

Here, so far as the referent of the phrase "scanning area" is an area capable of being scanned, the shape thereof can be any shape; for example, a line-shaped area on the target subject, or an area on the surface, etc. Further, for cases in which the target subject is an examination area that progresses in a direction moving deeper within a body cavity, etc., a ring-shaped area, or a cylindrical area are included in the referents of "scanning area".

Further, when "scanning the scanning area", the format of scanning can be any scanning format. For example, there are radial scanning formats wherein the scanning is performed by rotating a mirror installed at the distal end of a light guiding means for guiding the signal-wave, and linear scanning formats wherein the scanning is performed by moving the irradiation position of the signal-wave in a line form, etc.; in so far as a scanning format is capable of obtaining a tomographic image by use of a signal-wave, said scanning method can be employed. Note that also, any scanning method of scanning the signal-wave may be used; for example, there are scanning methods wherein the scanning is performed by moving the signal-wave emitting end, scanning methods wherein the scanning is performed by reflecting the signal-wave emitted from the emitting end by use of a controllable mirror or the like, of which the reflection direction thereof is capable of being controlled, and so on.

Further, the endoscope apparatus according to the present invention further comprises a tomographic image display means for displaying a tomographic image obtained by the tomographic image obtaining means, which can also be a means for concurrently displaying the target-subject image and the tomographic image.

Still further, the endoscope apparatus according to the present invention may also be an apparatus wherein: the position specifying means is a means for specifying two desired points; the scanning-area setting means is a means for setting as the scanning area an area on the target subject including the points thereon corresponding to the two points specified by the position specifying means; the tomographic image obtaining means is a means for obtaining a plurality of radial tomographic images; further comprising a 3-dimensional tomographic image forming means for forming a 3-dimensional radial tomographic image based on a plurality of radial tomographic images obtained by the tomographic image obtaining means.

Here, "radial tomographic image" refers to a tomographic image obtained by a radial scanning wherein the scanning direction of the signal-wave is rotated within a planar surface in a direction substantially perpendicular to the lengthwise direction of the insertion portion of the endoscope; more specifically, to a tomographic image showing a wall of the interior of the body cavity, into which the insertion portion has been inserted, in round cross-sections.

Further, the expression "sets as the scanning area an area on the target subject containing the points thereon corresponding to the two points specified by the position specifying means" refers to, for example, the setting of an area of the body cavity between the radial scanning range including a point on the target subject corresponding to a point specified by the position specifying means and the radial scanning range including another point on the target subject corresponding to another point specified by the position specifying means, as the scanning area.

Still further, the endoscope apparatus according to the present invention may also be an apparatus wherein: the position specifying means is a means for specifying three or more desired points; the scanning-area setting means is a means for setting as the scanning area an area on the target subject enclosed by the points thereon corresponding to the three or more points specified by the position specifying means; the tomographic image obtaining means is a means for obtaining a plurality of linear tomographic images; further comprising a 3-dimensional tomographic image forming means for forming a 3-dimensional linear tomographic image based on a plurality of radial tomographic images obtained by the tomographic image obtaining means.

Here, "linear tomographic image" refers to a tomographic image obtained by a linear scanning wherein the signal-wave is scanned in a line form, including, in addition to standard line-form scanning, cases in which a tomographic image is obtained by a partial radial scanning.

Further, the expression "sets as the scanning area an area on the target subject enclosed by the points thereon corresponding to the three or more points specified by the position specifying means" refers to, for example, in a case in which 3 points have been specified by the position specifying means, the setting of an area on the target subject enclosed by a plurality of points thereon corresponding to the three points specified by the position specifying means, as the scanning area.

Still further, when a 3-dimensional tomographic image is to be formed, the endoscope apparatus according to the present invention may also be an apparatus further comprising: a memory means for recording a pixel position on the target-subject image and the relation between said pixel position and a pixel position on a 3-dimensional optical tomographic image; a 3-dimensional position specifying means for specifying a desired point on the 3-dimensional tomographic image displayed on the tomographic image display means; and a 3-dimensional specified point display means for reading out from the memory means the pixel positions of the point specified by the 3-dimensional position specifying means and the point on the target-subject image corresponding thereto, and displaying the specified 3-dimensional position and the point corresponding thereto on the target-subject image. Here, "a 3-dimensional tomographic image" refers to a 3-dimensional radial tomographic image or a 3-dimensional linear tomographic image.

Note that as to the above-described position specifying means and 3-dimensional position specifying means, any means that can specify two desired points can be employed: For example, a pen-type interface for specifying two desired points by touching a display screen therewith; a means for entering the coordinates of two desired points; a mouse that operates as a cursor for inputting two desired points, or the like can be employed there as.

If the aforementioned signal-wave is a low-coherence light, an optical tomographic image obtaining means, which scans the scanning area with the low-coherence light and utilizes the reflected-light reflected from a predetermined depth of the scanning area and a reference-light having a slight difference in frequency with respect to the signal-light, for obtaining an optical tomographic image of the scanning area can be employed. Note that, if the target subject is a living-tissue subject, it is preferable that the low-coherence light is of a wavelength within the 600–1700 nm wavelength range.

If the aforementioned signal-wave is an ultrasonic wave, an ultrasound tomographic image obtaining means, which scans the scanning area with the ultrasonic wave and utilizes the reflected-wave reflected from a predetermined depth of the scanning area, for obtaining an ultrasound tomographic image of the scanning area can be employed. Note that, if the target subject is a living-tissue subject, it is preferable that the frequency of the ultrasonic wave is between 1 MHz and 50 MHz.

According to the endoscope apparatus of the present invention: one or more desired points are specified on a target-subject image displayed on the target-subject image display means, a scanning area to be scanned by the signal-wave is set based on the specified point(s), and the set scanning area is scanned with the signal-wave to obtain a tomographic image thereof; whereby the trouble of having to manually direct the signal-wave to a desired scanning area is eliminated, and because a tomographic image of a desired scanning area can be expediently obtained, a tomographic image of a desired scanning area can be obtained with a high degree of efficiency. Further, a tomographic image of a desired scanning area can be obtained with a high degree of accuracy.

Further, if the target-subject image and the tomographic image are displayed concurrently on the tomographic image display means for displaying a tomographic image, an operator can observe both the target-subject image and the tomographic image concurrently, whereby the overall convenience attained in the practical application of the endoscope apparatus is improved.

Still further, if the endoscope apparatus according to the present invention is an apparatus for setting as the scanning area an area on the target subject including the points thereon corresponding to the two desired points that have been specified, and forming a 3-dimensional radial tomographic image based on a plurality of radial tomographic images obtained by scanning this scanning area with the signal-wave, a 3-dimensional radial tomographic image of a desired area can be obtained with a high degree of efficiency.

In addition, if the endoscope apparatus according to the present invention is an apparatus for setting as the scanning area an area on the target subject enclosed by the points thereon corresponding to the three or more desired points that have been specified, and forming a 3-dimensional linear tomographic image based on a plurality of linear tomographic images obtained by scanning this scanning area with the signal-wave, a 3-dimensional linear tomographic image of a desired area can be obtained with a high degree of efficiency. Further, for cases in which a 3-dimensional tomographic image of a diseased portion that is limited to a localized area, etc., is to be obtained, a 3-dimensional tomographic image of only the area in the vicinity of the diseased portion can be obtained, and a 3-dimensional optical tomographic image is not obtained of unnecessary areas, whereby the radial 3-dimensional optical tomographic image can be obtained with a high degree of efficiency.

If the endoscope apparatus is an apparatus for specifying a desired 3-dimensional point on a 3-dimensional tomographic image, causing the point on the target subject corresponding to the 3-dimensional specified point to be displayed, the operator can easily confirm a desired point on the 3-dimensional optical tomographic image and the point corresponding thereto on the target subject image, whereby the overall convenience attained through the practical application of the endoscope apparatus can be further improved.

For cases in which the signal-wave is a low-coherence light, and the tomographic image obtaining means is an optical tomographic image obtaining means, which scans the scanning area with the low-coherence light and utilizes the reflected-light reflected from a predetermined depth of the scanning area and a reference-light having a slight difference in frequency with respect to the signal-light, for obtaining an optical tomographic image of the scanning area, a high-resolution tomographic image, which has a resolution corresponding to the coherence length of the low-coherence light, can be obtained. Note that, if the target subject is a living-tissue subject and the wavelength of the low-coherence light is within the 600–1700 nm wavelength range, the signal-light exhibits good transmittance and dispersion characteristics with respect to the living-tissue subject.

If the aforementioned signal-wave is an ultrasonic wave, and the tomographic image obtaining means is an ultrasound tomographic image obtaining means, which scans the scanning area with the ultrasonic wave and utilizes the reflected-wave reflected from a predetermined depth of the scanning area, for obtaining an ultrasound tomographic image of the scanning area, because an ultrasonic wave is capable of penetrating to deeper depths of a target subject in comparison to a signal-light or the like, a tomographic image of a deeper portion can be obtained. Note that, if the target subject is a living-tissue subject, and the frequency of the ultrasonic wave is between 1 MHz and 50 MHz, this ultrasonic wave exhibits good reflection characteristics with respect to the living-tissue subject.

BRIEF DESCRIPTION OF THE DRAWINGS

FIG. 4 illustrates a 3-dimensional linear tomographic image.

DESCRIPTION OF THE PREFERRED EMBODIMENTS

Figure 1:
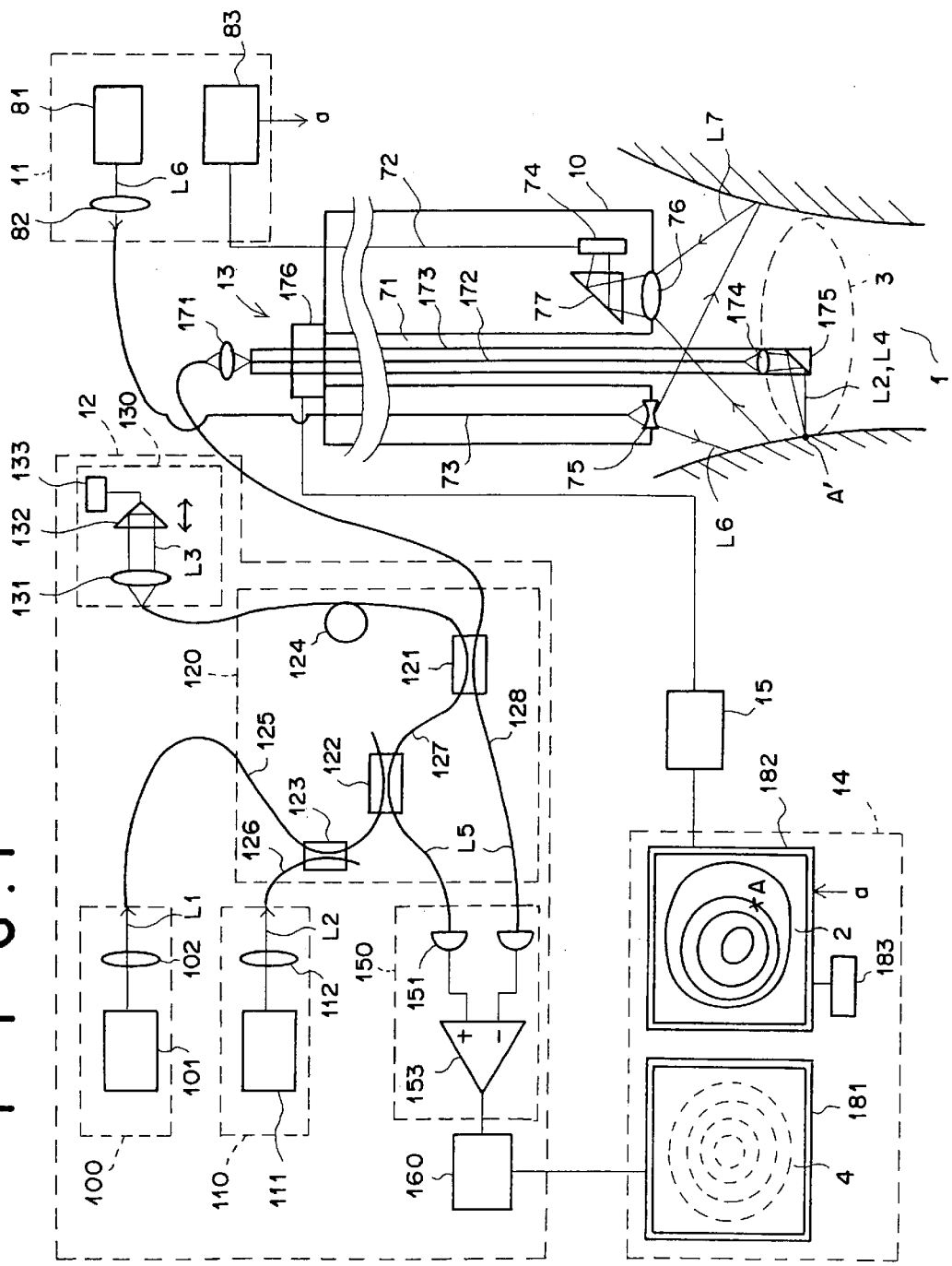
FIG. 1 is a schematic drawing of the first embodiment of the endoscope apparatus according to the present invention.
Figure 2:
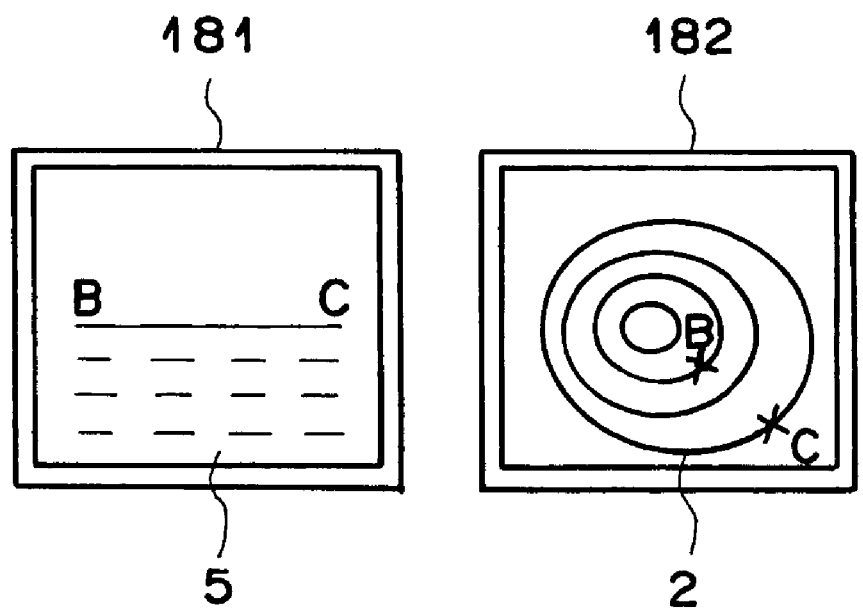
FIG. 2 illustrates a linear tomographic image.

Hereinafter a description of the preferred embodiments of the present invention will be explained with reference to the attached drawings. First, the first embodiment of the present invention will be explained with reference to FIG. 1 and FIG. 2. FIG. 1 is a schematic drawing of the endoscope apparatus, in its entirety, according to the first preferred embodiment of the present invention. FIG. 2 is a drawing showing the images displayed according to the current embodiment. This endoscope apparatus is an apparatus for obtaining and displaying a radial optical tomographic image 4 or a linear optical tomographic image 5 based on a desired point specified on a target-subject image 2, which is an image of the interior of a body cavity 1 of a patient.

The endoscope apparatus according to the current embodiment comprises an insertion portion 10 to be inserted into a body cavity 1 of a patient, a target-subject image obtaining portion 11 for obtaining a target-subject image 2 of the interior of the body cavity 1 of the patient, an OCT obtaining portion 12 for obtaining an optical tomographic image of a scanning area 3 within the body cavity 1, an OCT probe 13 to be inserted into the forceps insertion port 71 provided on the insertion portion 10, a display portion 14 for displaying a target-subject image 2 and a radial optical tomographic image or a linear tomographic image of the scanning area 3, and a scanning-area setting means 15 for setting a scanning area, based on a point specified on the target-subject image 2, to be scanned by a signal-light.

The insertion portion 10 comprises, a forceps insertion port 71 extending internally therethrough to the distal end thereof, a CCD cable 72 extending internally to the distal end thereof, and a light guide 73. A CCD photographing element 74 is connected to the distal end of the CCD cable 72. An illuminating lens 75 is provided at the distal end of the light guide 73, that is, at the distal end of the insertion portion 10. Further, an image obtaining lens 76 is provided at the distal end of the insertion portion 10, and a prism 77 is provided on the inner side of this image obtaining lens 76, that is, on the side of the image obtaining lens 76 opposite that facing toward the target subject.

The light guide 73 is formed of a composite glass fiber, and is connected to the target-subject image obtaining portion 11. The prism 77 reflects the reflected-light L7, which is the component of the white-light L6 that has been reflected from the body cavity 1 and focused by the image obtaining lens 76, causing said reflected-light L7 to enter the CCD photographing element 74.

The target-subject image obtaining portion 11 comprises a white-light source 81 that emits a white-light L6 for obtaining a target-subject image, a lens 82 that causes the white-light L6 emitted from said white-light source 81 to enter the light guide 73, and an image processing portion 83 for carrying out image processing on an image obtained by the CCD photographing element 74 and outputting the image signal formed thereby to the monitor 182, which is described below.

The OCT portion 12 comprises: a light source 100 for emitting a low-coherence light L1 having a core wavelength of 800 nm and a coherence length of 20 um; an aiming-light source 110 for emitting an aiming light L2, which is a visible light; a fiberoptics coupling system 120 for combining the low-coherence light L1 and the aiming-light L2, and separating and combining the reference-light L3 and the signal-light L4 of the low-coherence light L1; an optical path extending portion 130 disposed along the optical path of the reference-light L3, which causes the length of the optical path of said reference-light L3 to change; a balance differential detecting portion 150 for detecting the intensity of the interference-light L5 caused by the signal-light L4' reflected from a predetermined depth of the scanning area 3 and the reference-light L3; and a signal processing portion 160 for performing a heterodyne detection to obtain the intensity of the signal-light L4', which is the component of the signal-light L4 that has been reflected from a predetermined surface of the scanning area 3, from the intensity of the interference-light L5 detected by said balance differential detecting portion 150, and forming optical tomographic image data.

The light source 100 of the OCT portion 11 is provided with an SLD (Super Luminescent Diode) 101 for emitting a low-coherence light L1, and a lens 102 for focusing the low-coherence light L1 emitted from said SLD 101.

The aiming-light source 110 comprises a semiconductor laser 111 for emitting a green laser light as an aiming-light L2, and a lens 112 for focusing the aiming-light L2 emitted from said semiconductor laser 111.

The fiber optics coupling system 120 comprises: a fiber coupler 121 for separating the low-coherence light L1 emitted from the SLD 101 into a signal-light L4 and a reference-light L3, and combining the signal-light L4', which is the component of the signal-light L4 that has been reflected from the scanning area 3, and the reference-light L3 to obtain the interference-light L5; a fiber coupler 122 and a fiber coupler 123 provided between the light source portion 100 and the fiber coupler 121; a Piezo element 124 for causing a slight shift in the frequency of the reference-light L3; a fiber 125 for connecting the light source portion 100 and the fiber coupler 122; a fiber 126 for connecting the aiming-light source 110 and the fiber coupler 123; a fiber 127 for connecting the balance differential detecting portion 150 and the optical path extending portion 130, by way of the fiber couplers 121 and 122; and a fiber 128 for connecting the OCT probe 13 and the balance differential detecting portion 150 by way of the fiber coupler 121. Note that the fibers 125, 127, and 128 are single mode optical fibers.

The optical path extension portion 130 comprises: a lens 131 for converting the reference-light L3 emitted from the fiber 127 to a parallel light and for causing the reflected reference-light L3 to enter the fiber 127; a prism 132 which, by being moved in the horizontal direction indicated in FIG. 1, causes the length of the optical path of the reference-light L3 to change; and a drive unit 133 for moving said prism 132 in said horizontal direction.

The balance differential detecting portion 150 comprises a photodetector 151 and a photodetector 152 for measuring the intensity of the interference-light L5, and a differential amplifier 153 for adjusting the input balance of the detection values output by the photodetectors 151 and 152 and canceling out the noise component and drift component thereof, and then amplifying the difference therebetween.

The OCT probe 13 is provided with a coated tube 173 capable of being inserted into the forceps insertion port 171 of the insertion portion 10, and a fiber 172 which extends through said coated tube 173. A lens 174 for focusing the signal-light L4 emitted from the distal end of the fiber 172 and feeding back the signal-light L4', which is the component of the signal-light L4 reflected from the scanning area 3, to the fiber 172 is provided at the distal end of said fiber 172; a prism 175 for perpendicularly reflecting the signal-light L4 and the signal-light L4' is provided at the distal end further than said lens 174, that is, at the distal end of the OCT probe 13. A lens 171 for focusing and causing the signal-light L4 emitted from the fiber 128 to enter the fiber 172 and feeding back the signal-light L4' to the fiber 128 is provided at the rear end of the fiber 172, that is, at the connecting portion connecting the fiber 128 and the fiber 172. The fiber 172, the lens 174 and the prism 175 are installed fixedly within the coated tube 173. Further, a scanning control portion 176 for rotating and sliding the coated tube 173 is mounted on the base portion of the coated tube 173. The scanning control portion 176 is connected to the scanning area setting portion 15, and performs, based on the scanning area set at said scanning area setting portion, the radial or linear scanning of the scanning area with the signal-light L4 by sliding and rotating the coated tube 173.

The display portion 14 is provided with a monitor 181 as an optical tomographic image display means for displaying an optical tomographic image outputted by the OCT portion 12, a monitor 182 as a target-subject image display means for displaying a target-subject image outputted by the target-subject image obtaining portion 11, and a pen-type input portion 183 as a position specifying means for specifying a desired pixel position on the target-subject image. Note that each part is connected to a controller (not shown), which controls the operational timing thereof. Note that the OCT obtaining means 12 and the OCT probe 13 form the optical tomographic image obtaining means of the present invention.

Next, the operation of the endoscope apparatus that is the first embodiment of the present invention will be explained. First, the operator inserts the insertion portion 10 of the endoscope apparatus into a body cavity 1 of the patient, and a target-subject image 2 is displayed on the monitor 182. At this time, first, the white-light L6 emitted from the white-light source 81 of the target-subject image obtaining portion 11 enters the light guide 73 by way of the lens 82, and after being guided to the distal end of the insertion portion 10, said white-light L6 is projected onto the interior of the body cavity 1 by the illuminating lens 75.

The reflected-light L7 of the white-light L6 is focused by the image obtaining lens 76, reflected by the prism 107, and focused on the CCD photographing element 74. The obtained image signal, which has been photoelectrically converted by the CCD photographing element 74, is outputted to the image processing portion 83 via the CCD cable 72.

The image processing portion 83 first subjects the image signal obtained by the CCD photographing element 74 to signal processing such as amplification, 2-bit relative sampling, clamping, blanking, etc., and then computes an image signal and outputs said computed image signal to the monitor 182 in synchronization with a display timing.

While observing the target-subject image 2 displayed on the monitor 182, the operator manually moves the insertion portion to a desired section and observes the desired section.

Next, the operation occurring when a radial optical tomographic image 4 is to be obtained will be explained. The operator inserts the OCT probe 13 into the forceps insertion port 171 of the insertion portion 10. While observing the target-subject image 2 displayed on the monitor 182, the operator specifies on the target-subject image 2 image displayed on the monitor 182, by use of the pen-type position input means 183, a point A for obtaining a radial tomographic image.

At this time, a green aiming-light L2 is concurrently emitted from the semiconductor laser 111 of the aiming light source 110. Said aiming-light L2 is focused by the lens 112 and enters the fiber 126. The aiming-light L2 is guided through the fiber 126, the fiber coupler 123, the fiber 125, the fiber coupler 122, the fiber 127, the fiber coupler 121 and the fiber 128, and enters the fiber 172 via the lens 171. The aiming-light L2 emitted from the fiber 172 is focused by the lens 174, reflected by the prism 175, and projected onto the interior of the body cavity 1 as a green spot light. The reflected-light of this aiming-light L2 is also displayed on the monitor 182 as a bright point within the target-subject image 2 displayed thereon.

The scanning area setting portion 15 computes the position of the point A specified on the target-subject image 2 relative to the obtained bright point of the reflected-light of the aiming-light L2, and causes, by sliding and rotating the coated tube 173 under the control of the scanning control portion 176, the bright point of the aiming-light L2 to be aligned with the point A specified on the target-subject image 2. According to the operation described above, a starting scanning point A' on the interior of the body cavity 1 for the operation occurring when a radial optical tomographic image is to be obtained is set, and the radial optical tomographic image of the scanning area 3 including said starting scanning point A' is obtained.

When the starting scanning point A' has been set, the low-coherence light L1 having a core wavelength of 800 nm and a coherence length of 20 um is emitted from the SLD 101. Said low-coherence light L1 is focused by the lens 102 and enters the fiber 125.

The low-coherence light L1 that has passed through the fiber 125 enters the fiber 127 at the fiber coupler 122. Said low-coherence light L1 is separated, at the fiber coupler 121, into the reference-light L3, which proceeds within the fiber 127 toward the optical path extending portion 130, and the signal-light L4, which proceeds within the fiber 128 toward the OCT probe 13.

The reference-light L3 is modulated by the Piezo element 124 provided along the optical path, causing a slight difference in frequency $\Delta f$ to occur between the reference-light L3 and the signal-light L4.

The signal-light L4 is projected onto the starting scanning point A' of the interior of the body cavity 1 by way of the lens 171 of the OCT probe 13, the fiber 172, the lens 174 and the prism 175. The signal-light L4', which is the component of the signal-light L4 entering the starting scanning point A' that has been reflected at a predetermined depth thereof, is fed back to the fiber 128 by way of the prism 175, the lens 174 the fiber 172 and the lens 171. The signal-light L4' fed back to the fiber 128 is combined within the fiber coupler 121 with the reference-light L3 fed back to the fiber 127, which is described below.

On the other hand, the reference-light L3 that has been modulated by the Piezo element 124 passes through the fiber 127 and enters the prism 132 through the lens 131 of the optical path extending portion 130. Said modulated reference-light L3 is then reflected by the prism 132 and is again transmitted by the lens 131 and fed back to the fiber 127. The reference-light L3 fed back to the fiber 127 is combined in the fiber coupler 121 with the signal-light L4' described above.

The signal-light L4' and the reference-light L3 combined in the fiber coupler 121 are again combined along the same axis and at a predetermined timing, and interference is caused between said signal-light L4' and reference-light L3, whereby said signal-light L4' and reference-light L3 become an interference-light L5, and a beat signal is produced.

Because the signal-light L4' and the reference-light L3 are low-coherence light of a short interference-susceptibility distance, after the low-coherence light has been separated into the signal-light L4 and the reference-light L3, if the length of the optical path of the signal-light L4 (L4') up to the point at which said signal-light L4 (L4') arrives at the fiber coupler 121 is substantially the same as the length of the optical path of the reference-light L3 up to the point at which said reference-light L3 arrives at the fiber 151, both of said lights interfere with each other, said interference repeats and generates a beat signal in a strong-weak cycle according to the difference (Δf) between the frequencies of the reference-light L3 and the signal-light L4.

The interference-light L5 is separated in the fiber coupler 121: one of the separated components thereof enters the photodetector 151 of the balance differential detector 150 after passing through the fiber 127; and the other of the separated components thereof enters the photodetector 152 after passing through the fiber 128.

The photodetectors 151 and 152 detect the signal strength of the beat signal from the interference-light L5, and the differential amplifier 153 obtains the difference between the detection value of the photodetector 151 and the detection value of the photodetector 152 and outputs said difference to the signal processing portion 160. Note that because the differential amplifier 153 is provided with a function for adjusting the balance of the direct current component of the value input thereto, even in a case, for example, in which drift occurs in the low-coherence light emitted from the light source portion 100, by amplifying the difference after adjusting the balance of the direct current component, the drift component is cancelled out, and only the beat signal is detected.

Note that at this time, the prism 132 is moved in the direction of its optical axis (the horizontal direction appearing in FIG. 1) by the drive portion 133. The length of the optical path of the reference-light L3 up to the point at which said reference-light L3 arrives at the fiber coupler 121 is changed thererby. Because the length of the optical path of the signal-light L4 (L4'), which interferes with the reference-light L3, also changes, the depth at which the tomographic data is obtained changes.

According to the operation described above, the tomographic data from the point on the surface of the interior of the body cavity 1 corresponding to the starting scanning point A' to a desired depth is obtained. Further, when the measurement occurring at the starting scanning point A' is completed, the scanning control portion 176 slightly rotates the coated tube 173 to another point within the scanning area 3 slightly removed from the starting scanning point A', and the tomographic data is obtained to a predetermined depth at this new point in the same manner. The above-described operation, wherein the coated tube 173 is rotated a microscopic distance and the tomographic data at each point is obtained, is repeated until the scanning of the scanning area is completed, that is, until the starting scanning point A' is returned to.

The signal processing portion 160 performs a heterodyne detection to obtain the intensity of the signal-light L4' reflected from a predetermined surface of each scanning point from the intensity of the interference-light L5 detected by the balance differential detecting portion 150, converts the obtained intensity of the signal-light L4' to a radial optical tomographic image, and outputs said radial optical tomographic image to the monitor 181.

The monitor 181 displays the radial optical tomographic image 4 outputted from the signal processing portion 160. According to this type of operation, a radial optical tomographic image 4 of the body cavity 1 shown in round cross-sections can be displayed.

Next, the operation occurring when a linear optical tomographic image 5 such as that shown in FIG. 2 is to be obtained will be explained. When a linear optical tomographic image is to be obtained, the operator inserts the OCT probe 13 into the forceps insertion port 71, in the same manner as when a radial optical tomographic image is to be obtained. While observing the target-subject image 2 displayed on the monitor 182, the operator specifies, by use of the pen-type position input means 183, on the target-subject image 2 image displayed on the monitor 182 a starting scanning point B and a finishing scanning point C for the operation to obtain a linear optical tomographic image.

When the aiming-light L2 is projected onto the interior of the body cavity 1, the reflected-light of said aiming-light L2 is displayed as a bright point on the target-subject image 2 displayed on the monitor 182.

The scanning area setting portion 15 first computes the position of the starting scanning point B specified on the target-subject image 2 relative to the bright point of the reflected-light of the aiming-light L2, and aligns the bright point of the aiming-light L2 with said starting scanning point B by sliding and rotating the coated tube 173 under the control of the scanning control portion 176. When said two points have been aligned, the scanning control portion 176 records the position which is illuminated by the aiming-light L2, that is, the angle and slide position of the coated tube 173 relative to the starting scanning point. Then, the scanning area specifying portion 15 computes the position of the finishing scanning point C relative to the bright point of the reflected-light of the aiming-light L2, and in the same manner as described above, aligns the bright point of the aiming-light L2 with said finishing scanning point C by sliding and rotating the coated tube 173 under the control of the scanning control portion 176. When said two points have been aligned, the scanning control portion 176 records the position which is illuminated by the aiming-light L2, that is, the angle and slide position of the coated tube 173 relative to the finishing scanning point. According to the operation described above, the starting scanning point B and the finishing scanning point C within the body cavity 1 for the operation occurring when a radial optical tomographic image is to be obtained are set, and the linear optical tomographic image of the area between said starting scanning point B and said finishing scanning point C is obtained.

First, the scanning control portion 176 controls the angle and the slide position of the coated tube 173 so that the signal-light L4 is projected onto the starting scanning point within the body cavity 1. Then, by the same operation occurring when a radial optical tomographic image is to be obtained, the tomographic data is obtained from the point on the surface of the body cavity 1 corresponding to the starting scanning point to a desired depth. Further, when the measurement occurring at the starting scanning point has been completed, the scanning control portion 176 controls the angle and the slide position of the coated tube 173 so as to move the position irradiated by the signal-light L4 (hereinafter referred to simply as the irradiation position) from the starting scanning position toward the finishing scanning position. Then, the tomographic data is obtained in the same manner at a new point a slight distance from the starting scanning position of the body cavity 1. This type of operation, in which the irradiation position of the signal-light L4 is moved in slight increments and the tomographic data obtained at each point new, is repeated until the finishing scanning point is reached. The signal processing portion 160 performs a heterodyne detection to obtain the intensity of the signal-light L4' reflected from a predetermined surface of each scanning area point from the intensity of the interference-light L5 detected by the balance differential detecting portion 150, converts the obtained intensity of the signal-light L4' to a linear optical tomographic image, and outputs said linear optical tomographic image to the monitor 181. The monitor 181 displays the obtained linear optical tomographic image 5.

According to the type of operation described above, wherein a single point A is set on the target-subject image 2 and a scanning area 3 is set based on this specified point A, because a radial optical tomographic image 4 of the scanning area 3 is obtained by scanning said scanning area 3 with the signal-light L4, the trouble of having to manually direct the signal-light L4 onto a desired scanning area is eliminated, whereby an optical tomographic image can be obtained expediently and a radial optical tomographic image of a desired scanning area can be obtained with a high degree of efficiency. Further, a radial optical tomographic image of a desired scanning area can be obtained accurately.

Further, a starting scanning point B and a finishing scanning point C are set on the target-subject image 2, and by setting the area of the body cavity 1 corresponding to these two specified points, B and C, as a scanning area, because a linear optical tomographic image is obtained by scanning this scanning area with the signal-light L4, the trouble of having to manually direct the signal-light L4 onto a desired scanning area is eliminated, whereby an optical tomographic image can be obtained expediently and a linear optical tomographic image of a desired scanning area can be obtained with a high degree of efficiency. Further, a linear optical tomographic image of a desired section can be obtained accurately.

Still further, if the target-subject image 2 and the radial optical tomographic image 4 or the linear optical tomographic image 5 are displayed concurrently, an operator can observe the target-subject image 2 and the radial optical tomographic image 4 or the linear optical tomographic image 5 concurrently, whereby the overall convenience attained in the practical application of the endoscope apparatus is improved.

Note that according to the current embodiment, although a radial optical tomographic image 4 and a linear optical tomographic image 5 are obtained and displayed, as an alternative embodiment, only a radial optical tomographic image 4 or only a linear optical tomographic image 5 can be obtained and displayed.

Figure 3:
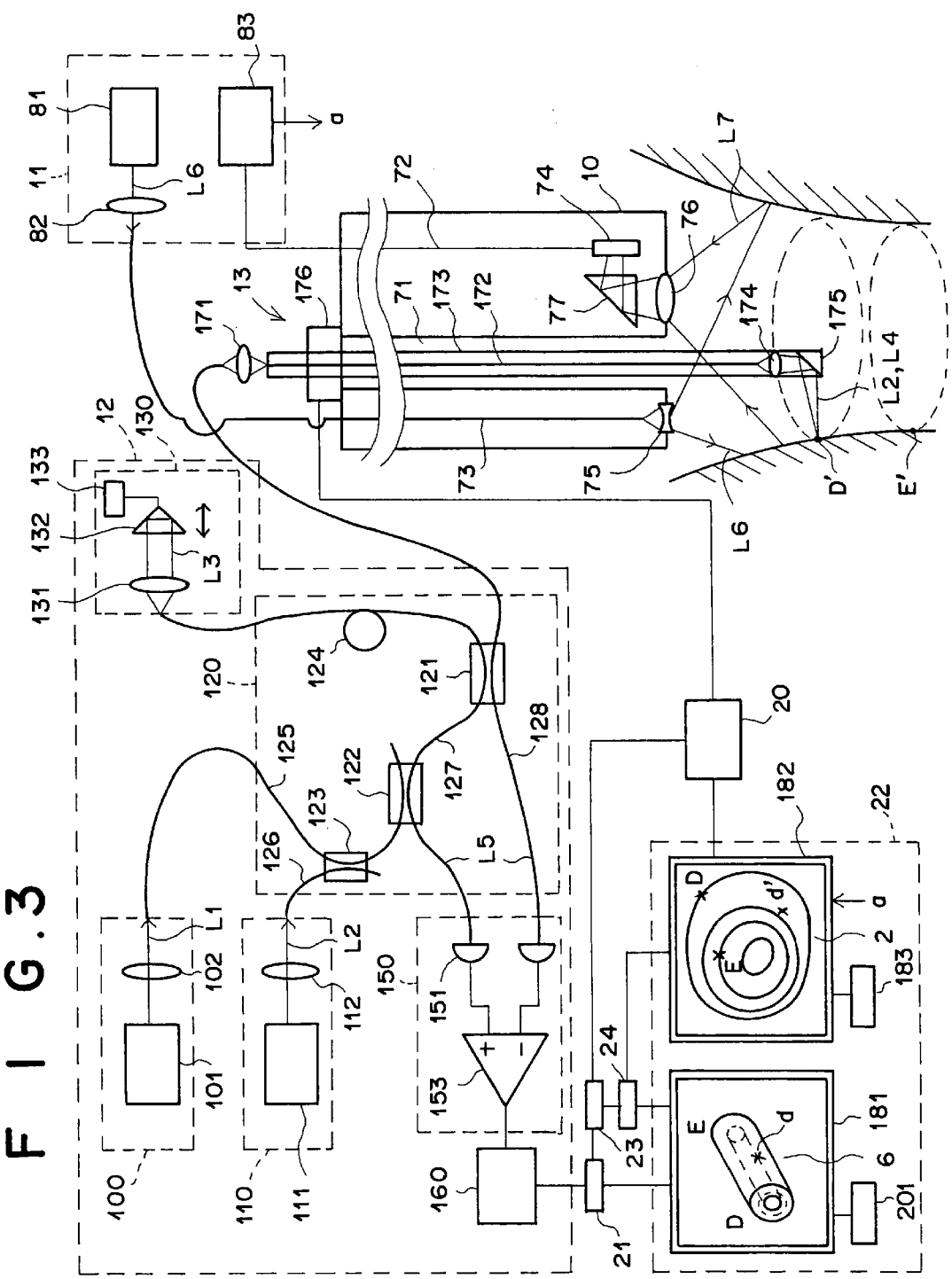
FIG. 3 is a schematic drawing of the second embodiment of the endoscope apparatus according to the present invention.

Next, the second embodiment of the present invention will be explained with reference to FIG. 3 and FIG. 4. FIG. 3 is a schematic drawing of the endoscope apparatus, in its entirety, according to the second embodiment of the present invention. FIG. 4 is a drawing illustrating the images displayed according to the current embodiment. This endoscope apparatus is an apparatus for obtaining and displaying a 3-dimensional radial optical tomographic image 6 of the section of the interior of the body cavity between two points specified on the target-subject image 2, or a 3-dimensional linear optical tomographic image 7 of the area of the interior of the body cavity enclosed by four points specified on the target-subject image 2; further, this endoscope apparatus is an apparatus for displaying a 3-dimensional point that has been specified on the 3-dimensional radial optical tomographic image 6 or the 3-dimensional linear optical tomographic image 7 and which corresponds to a point on the target-subject image 2.

The endoscope apparatus according to the current embodiment comprises an insertion portion 10 to be inserted into a body cavity 1 of a patient, a target-subject image obtaining portion 11 for obtaining a target-subject image 2 of the interior of the body cavity 1 of the patient, an OCT obtaining portion 12 for obtaining an optical tomographic image of the interior of the body cavity 1, an OCT probe 13 to be inserted into the forceps insertion port 71 provided on the insertion portion 10, a scanning-area setting portion 20 for setting a scanning area, based on points specified on the target-subject image 2, a 3-dimensional optical tomographic image forming portion 21 for forming a 3-dimensional optical tomographic image from a plurality of optical tomographic images, a display portion 22 for displaying a target-subject image 2 and a 3-dimensional radial optical tomographic image 6 or a 3-dimensional linear optical tomographic image 7 of the interior of the body cavity 1, a memory portion 23 for recording the relation between a pixel position on the target-subject image 2 and a pixel position on a 3-dimensional optical tomographic image, and a 3-dimensional specified point display portion 24 for displaying a 3-dimensional point specified on a 3-dimensional optical tomographic image and the point corresponding thereto on the target-subject image. Note that elements in common with the first embodiment shown in FIG. 1 are likewise labeled, and in so far as it is not particularly required, further explanation thereof has been omitted.

When a 3-dimensional radial optical tomographic image is to be obtained, the scanning area setting portion 20 sets a cylindrical area of the body cavity including the points of the target subject corresponding to the two points specified on the target-subject image as the scanning area. Further, when a 3-dimensional linear optical tomographic image is to be obtained, the area enclosed by the four points on the target subject corresponding to the points specified on the target-subject image is set as the scanning area.

The 3-dimensional optical tomographic image forming portion 21 is provided with a memory portion (not shown) for storing a plurality of optical tomographic images outputted by the OCT obtaining portion 12. Said 3-dimensional optical tomographic image forming portion 21 forms a 3-dimensional optical tomographic image based on the plurality of optical tomographic images stored in said memory portion, and outputs the formed 3-dimensional optical tomographic image to the display portion 22.

The display portion 22 is provided with a monitor 181 for displaying a 3-dimensional optical tomographic image outputted from the 3-dimensional optical tomographic image forming portion 21, a monitor 182 for displaying a target-subject image 2, a pen-type inputting portion 183 for specifying a desired pixel position on the target-subject image 2, a pen-type inputting portion 201 as a 3-dimensional position specifying means for specifying a desired pixel position on a 3-dimensional optical tomographic image. Note that each part is connected to a controller (not shown), which controls the operational timing thereof.

Next, the operation of the endoscope apparatus according to the second embodiment of the present invention will be explained. In the same manner as in the first embodiment, first, a target-subject image 2 is obtained and displayed on the monitor 182. While observing the target-subject image 2 displayed on the monitor 182, the operator manually moves the insertion portion to a desired section and observes the desired section.

First, the operation occurring when a 3-dimensional radial optical tomographic image 6 is to be obtained will be explained. When a 3-dimensional radial optical tomographic image 6 is to be obtained, the operator inserts the OCT probe 13 into the forceps insertion port 171 of the insertion portion 10. While observing the target-subject image 2 displayed on the monitor 182, the operator specifies, by use of the pen-type position input means 183, on the target-subject image 2 image displayed on the monitor 182 a starting scanning point D and a finishing scanning point E that define the scanning area for obtaining a 3-dimensional radial tomographic image.

When the aiming-light L2 is projected onto the interior of the body cavity 1, the reflected-light of said aiming-light L2 is also displayed on the monitor 182 as a bright point on the target-subject image 2 displayed thereon.

The scanning area setting portion 20 first computes the position of the starting scanning point D specified on the target-subject image 2 relative to the bright point of the reflected-light of the aiming-light L2, and aligns the bright point of the aiming-light L2 with said starting scanning point D by sliding and rotating the coated tube 173 under the control of the scanning control portion 176. When said two points have been aligned, the scanning control portion 176 records the angle and slide position of the coated tube 173 corresponding to the position illuminated by the aiming-light L2 (herein after referred to simply as the illumination position), that is, to the starting scanning point position D'. Then, the scanning area specifying portion 20 computes the position of the finishing scanning point E relative to the bright point of the reflected-light of the aiming-light L2, and in the same manner as described above, aligns the bright point of the aiming-light L2 with said finishing scanning point E by sliding and rotating the coated tube 173 under the control of the scanning control portion 176. When said two points have been aligned, the scanning control portion 176 records the angle and slide position of the coated tube 173 corresponding to the illumination position of the aiming-light L2, that is, to the starting scanning point position E'. According to the operation described above, the starting scanning point D' and the finishing scanning point E' within the body cavity 1 for the operation occurring when a 3-dimensional radial optical tomographic image is to be obtained are set, and the cylindrical area including said starting scanning point D' and finishing scanning point E' is set as the scanning area.

Next, the scanning control portion 176 controls the angle and the slide position of the coated tube 173 so that the signal-light L4 is projected onto the starting scanning point D' within the body cavity 1. Then, by the same operation occurring when a radial optical tomographic image is to be obtained according to the first embodiment, a radial optical tomographic image including the starting scanning position D' is obtained. This radial optical tomographic image is temporarily stored in the 3-dimensional optical tomographic image forming portion 21.

When the radial optical tomographic image including the starting scanning position D' has been obtained, the scanning control portion 176 controls the slide position of the coated tube 173 so that the irradiation position of the signal-light L4 is moved from the starting scanning point D' toward the finishing scanning point E', that is, toward the interior. Then, a radial optical tomographic is obtained at this new point and stored in the 3-dimensional optical tomographic image forming portion 21. This type of operation is repeated until the radial optical tomographic image including the finishing scanning point E' is obtained.

After all of the radial optical tomographic images of the cylindrical scanning area, from the starting scanning point D' to the finishing scanning point E', have been obtained, the 3-dimensional optical tomographic image forming portion 21 forms a 3-dimensional radial optical tomographic image from these stored radial optical tomographic images, and outputs the formed 3-dimensional radial optical tomographic image to the monitor 181 of the display portion 22.

The monitor 181 displays the formed 3-dimensional radial optical tomographic image 6.

Further, at this time, the memory portion 23 records the relation between the pixel positions on the target-subject image 2 and the pixel positions on a 3-dimensional radial optical tomographic image 6 corresponding thereto.

While observing the 3-dimensional radial optical tomographic image 6 displayed on the monitor 181, the operator specifies, by use of the pen-type position specifying portion 201, a desired 3-dimensional point d, and the 3-dimensional specified point display means 24 reads out from the memory portion 23 the pixel position on the target-subject image corresponding to the 3-dimensional specified point don the 3-dimensional radial optical tomographic image 6, and displays a point D' of the target-subject image corresponding to the 3-dimensional specified point d.

Next, the operation occurring when a 3-dimensional linear optical tomographic image 7 is to be obtained will be explained. While observing a target-subject image 2 displayed on the monitor 182, the operator specifies, by use of the pen-type position input means 183, four points F, G, H, and I on the target-subject image 2 image displayed on the monitor 182, which define the scanning area for obtaining a 3-dimensional linear tomographic image, as shown in FIG. 4.

When the aiming-light L2 is projected onto the interior of the body cavity 1, the reflected-light of said aiming-light L2 is displayed as a bright point on the target-subject image 2 displayed on the monitor 182.

The scanning area setting portion 20 first computes the position of the point F specified on the target-subject image 2 relative to the bright point of the reflected-light of the aiming-light L2, and aligns the bright point of the aiming-light L2 with said specified point F by sliding and rotating the coated tube 173 under the control of the scanning control portion 176. When said two points have been aligned, the scanning control portion 176 records the angle and slide position of the coated tube 173 corresponding to the illumination position of the aiming-light L2. In the same manner, when each of specified points G, H, and I have been aligned with the bright point of the aiming-light 2, the scanning control portion 176 records the angle and slide position of the coated tube 173 corresponding to each respective illumination position of the aiming-light L2. Then, the area of the interior of the body cavity 1 enclosed by the points corresponding to each specified point is set as the scanning area.

Next, the scanning control portion 176 slides the coated tube 173 within the scanning area at one end of the scanning area, and the OCT obtaining portion 12 obtains a linear optical tomographic image, which is then stored in the 3-dimensional optical tomographic image forming portion 21. Then, the scanning control portion 176 rotates the coated tube 173 slightly, and again slides the coated tube 173 within the scanning area, whereby the OCT obtaining portion 12 obtains a linear optical tomographic image and stores the obtained linear optical tomographic image in the 3-dimensional optical tomographic image forming portion 21. The 3-dimensional optical tomographic image forming portion 21 forms a 3-dimensional optical tomographic image from these stored linear optical tomographic images, and outputs the formed 3-dimensional optical tomographic image to the monitor 181 of the display portion 22. The monitor 181 displays a 3-dimensional optical tomographic image as shown in FIG. 4.

Further, at this time, the memory portion 23 records the relation between the pixel positions on the target-subject image 2 and the pixel positions corresponding thereto on the 3-dimensional linear optical tomographic image 7.

While observing the 3-dimensional linear optical tomographic image 7 displayed on the monitor 181, the operator specifies, by use of the pen-type position specifying portion 201, a desired 3-dimensional point f, and the 3-dimensional specified point display means 24 reads out from the memory portion 23 the pixel position on the target-subject image corresponding to the 3-dimensional specified point f on the 3-dimensional linear optical tomographic image 7, and displays a point f' of the target-subject image corresponding to the 3-dimensional specified point f.

According to the operation described above, the cylindrical area of the body cavity including the two points specified by the inputting portion 201 is set as the scanning area, and because a radial 3-dimensional optical tomographic image is formed and displayed based on the plurality of radial optical tomographic images obtained by repeating the radial scanning of the scanning area with the signal-light L4, a radial 3-dimensional optical tomographic image of a desired area of the body cavity 1 can be obtained with a high degree of efficiency.

Further, the area enclosed by the four points F, G, H, and I, which have been specified by use of the inputting portion 183, is set as the scanning area, and because a linear 3-dimensional optical tomographic image is formed and displayed based on the plurality of linear optical tomographic images obtained by repeating the linear scanning of the scanning area with the signal-light L4, a linear 3-dimensional optical tomographic image of a desired area of the body cavity 1 can be obtained with a high degree of efficiency. Further, for cases in which the diseased portion is limited to a localized area, etc., a 3-dimensional optical tomographic image of only the area in the vicinity of the diseased portion can be obtained, and because a 3-dimensional optical tomographic image is not obtained of unnecessary areas, the radial 3-dimensional optical tomographic image can be obtained with a high degree of efficiency.

If the endoscope apparatus is an apparatus wherein, by specifying a desired 3-dimensional point on a 3-dimensional optical tomographic image, the point on the target-subject image 2 corresponding to the 3-dimensional specified point is displayed, the operator can easily confirm the state of a desired point on a 3-dimensional optical tomographic image and the point corresponding thereto on the target-subject image 2, whereby the overall convenience attained through the practical application of the endoscope apparatus can be further improved.

Note that, although according to the current embodiment a 3-dimensional radial optical tomographic image and a 3-dimensional linear optical tomographic image are obtained and displayed, as an alternative embodiment, only a 3-dimensional radial optical tomographic image or a 3-dimensional linear optical tomographic image can be obtained and displayed. Further, the current embodiment may be provided with a function for displaying the radial optical tomographic image or the linear optical tomographic occurring in the first embodiment.

Further, in each of the above-described embodiments, because the wavelength of the low-coherence light is 800 nm, the signal-light L4 exhibits good transmittance and dispersion characteristics with respect to the scanning area, whereby an optical tomographic image of a desired scanning area can be obtained.

Still further, although a green visible light has been employed as the aiming-light L2, if a photographing element capable of obtaining an image of light having a wavelength of 800 nm is used as the CCD photographing element 74, the signal-light L4 can be utilized as the aiming-light, whereby the aiming-light source becomes unnecessary and the configuration of the OCT obtaining means 12 can be simplified.

Figure 5:
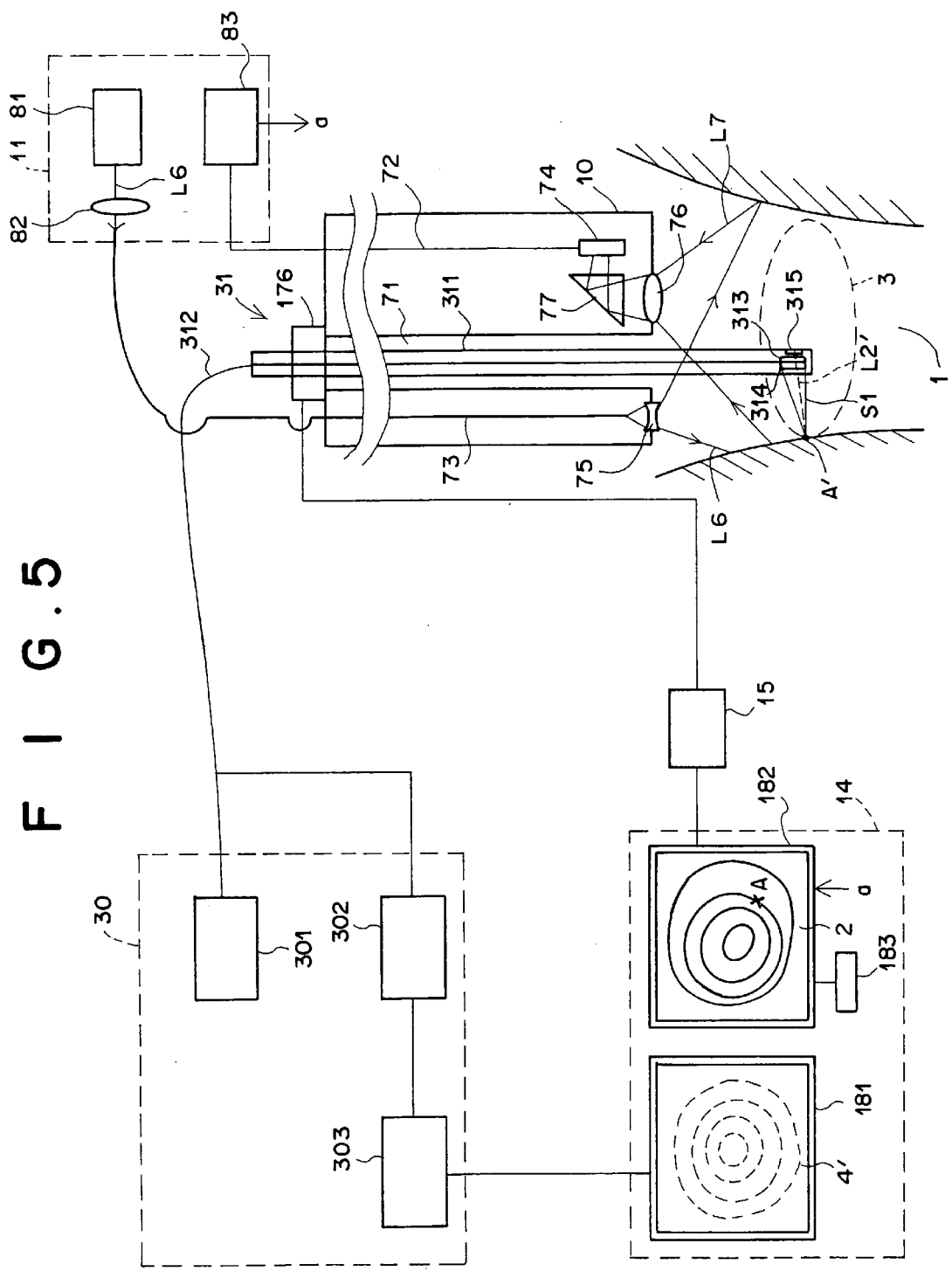
FIG. 5 is a schematic drawing of the third embodiment of the endoscope apparatus according to the present invention.
Figure 6:
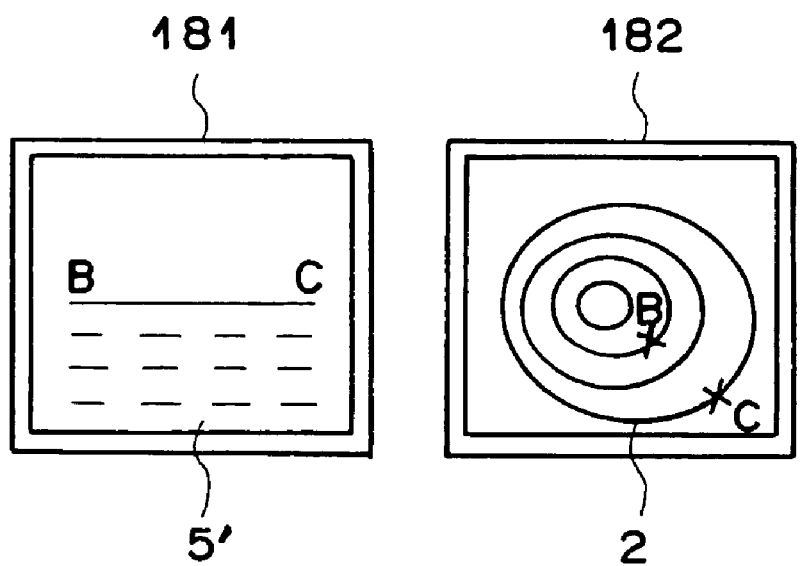
FIG. 6 illustrates a linear ultrasound tomographic image.

Next, the third embodiment of the present invention will be explained with reference to FIG. 5 and FIG. 6. FIG. 5 is a schematic drawing of the endoscope apparatus, in its entirety, according to the third embodiment of the present invention. FIG. 6 is a drawing illustrating the images displayed according to the current embodiment. This endoscope apparatus has an ultrasonic tomographic image obtaining apparatus built into said endoscope apparatus, and is an apparatus for obtaining and displaying a radial ultrasound tomographic image 4' or a linear ultrasound tomographic image 5' based on a desired point specified on a target-subject image 2, which is an image of the interior of a body cavity 1 of a patient.

The endoscope apparatus according to the current embodiment comprises an insertion portion 10 to be inserted into a body cavity 1 of a patient, a target-subject image obtaining portion 11 for obtaining a target-subject image 2 of the interior of the body cavity 1 of the patient, an ultrasonic-image obtaining portion 30 for obtaining an ultrasound tomographic image of a scanning area 3 within the body cavity 1, an ultrasonic probe 31 to be inserted into the forceps insertion port 71 provided on the insertion portion 10, a display portion 14 for displaying a target-subject image 2 and a radial ultrasound tomographic image or a linear ultrasound tomographic image of the scanning area 3, and a scanning-area setting portion 15 for setting a scanning area, based on the point(s) specified on the target-subject image 2, to be scanned by an ultrasonic wave. Note that elements in common with the first embodiment shown in FIG. 1 are likewise labeled, and in so far as it is not particularly required, further explanation thereof has been omitted.

The ultrasonic image obtaining portion 30 comprises transmitting portion 301 for transmitting a pulse type electric signal to the ultrasonic probe 31, a receiving portion 302 for amplifying and performing amplitude detection on the echo signal received at the ultrasonic probe 31, and a signal processing portion 303 for converting the amplitude signal detected by the receiving portion 302 to image data.

The ultrasonic probe 31 comprises a coated tube 311 capable of being inserted into the forceps insertion port 71 of the insertion portion 10 and a cable 312 extending internally therethrough. The pulse type electric signal received by the ultrasonic probe 31 is converted to a 20 MHz ultrasonic wave S1 at the distal end of the cable 312; said ultrasonic wave S1 is projected in a predetermined direction. Also, the ultrasonic probe 31 is further provided with: an ultrasonic transducer 313 for receiving an echo S2 produced at the position irradiated by the ultrasonic wave S1, and converting said echo S2 to an electric signal; an acoustic lens 314 for focusing the ultrasonic wave S1; and a semiconductor laser 315 for projecting an aiming-light onto substantially the same point as the ultrasonic wave irradiation point. Note that this ultrasonic transducer 313 is provided fixedly installed within the coated tube 311. Further, a scanning control portion 176 for sliding and rotating the coated tube 311 is mounted on the base portion of the coated tube 311. The scanning control portion 176 is connected to the scanning area setting portion 15, and performs, based on the scanning area set by said scanning area setting portion 15, the radial or linear scanning of the scanning area with the ultrasonic wave S1 by sliding and rotating the coated tube 311. Note that each part is connected to a controller (not shown), which controls the operational timing thereof. Further, the semiconductor laser 315 is connected to the controller by a cable (not shown). Note that the ultrasonic image obtaining portion 30 and the ultrasonic probe 31 form the ultrasound tomographic image obtaining means of the present invention.

Next, the operation of the endoscope apparatus that is the third embodiment of the present invention will be explained. First, the operator inserts the insertion portion 10 of the endoscope apparatus into a body cavity 1 of the patient, and a target-subject image 2 is displayed on the monitor 182. While observing the target-subject image 2 displayed on the monitor 182, the operator manually moves the insertion portion 10 so as to position said insertion portion 10 at a desired section, and observes the desired section.

When a radial ultrasound tomographic image 4' is to be obtained, the operator inserts the ultrasonic probe 31 into the forceps insertion port 171 of the insertion portion 10. While observing the target-subject image 2 displayed on the monitor 182, the operator specifies on the target-subject image 2 image displayed on the monitor 182, by use of the pen-type position input means 183, a point A for obtaining an ultrasound tomographic image.

At this time, a green aiming-light L2' is concurrently emitted from the semiconductor laser 315 for emitting an aiming-light. Said aiming-light L2 is projected onto the interior of the body cavity 1 as a green spot light. The reflected-light of this aiming-light L2 is also displayed on the monitor 182 as a bright point within the target-subject image 2 displayed thereon.

The scanning area setting portion 15 computes the position of the point A specified on the target-subject image 2 relative to the obtained bright point of the reflected-light of the aiming-light L2', and causes, by sliding and rotating the coated tube 173 under the control of the scanning control portion 176, the bright point of the aiming-light L2' to be aligned with the point A specified on the target-subject image 2. According to the operation described above, a starting scanning point A' on the interior of the body cavity 1 for the operation occurring when a radial ultrasound tomographic image is to be obtained is set, and the radial ultrasound tomographic image of the scanning area 3 including said starting scanning point A' is obtained.

The pulse type electric signal outputted from the transmitting portion 310 is transmitted via the cable 312 to the ultrasonic transducer 313, and converted to an ultrasonic wave S1. The ultrasonic wave S1 emitted from the ultrasonic transducer 313 is focused by the acoustic lens and projected onto the starting scanning point A'. The echo S2 produced at a deep portion of the starting scanning point A' is received by the ultrasonic transducer 313, converted again to an electric signal, and transmitted to the receiving portion 312. Because this electric signal is a very weak signal, said signal is amplified at the receiving portion 302, and then subjected to amplitude detection. The detected amplitude signal is outputted to the signal processing portion 303. According to the operation described above, the ultrasonic tomographic data of starting scanning point A' of the interior of the body cavity 1 is obtained. Further, when the measurement occurring at the starting scanning point A' is completed, the scanning control portion 176 slightly rotates the coated tube 311 to another point within the scanning area 3 slightly removed from the starting scanning point A', and the ultrasonic tomographic data is obtained at the new point in the same manner. The above-described operation, wherein the coated tube 311 is rotated a microscopic distance and the tomographic data at each new point is obtained, is repeated until the scanning of the scanning area is completed, that is, until the starting scanning point A' is returned to.

The signal processing portion 303 converts the amplitude signal of the echo outputted from the receiving portion 302 to ultrasound tomographic image data, and outputs said ultrasound tomographic image data to the monitor 181. The monitor 181 displays as a radial ultrasound tomographic image 4' the ultrasound tomographic image data outputted from the signal processing portion 303. According to this type of operation, a radial ultrasound tomographic image 4' of the body cavity 1 shown in round cross-sections can be displayed.

According to the type of operation described above, wherein a single point A is set on the target-subject image 2 and a scanning area 3 is set based on this point A, because a radial ultrasound tomographic image 4' of the scanning area 3 is obtained by scanning said scanning area 3 with the ultrasonic wave S1, the trouble of having to manually direct the irradiation position of the ultrasonic wave S1 onto a desired scanning area is eliminated, whereby an ultrasound tomographic image can be obtained expediently and a radial ultrasound tomographic image of a desired scanning area can be obtained with a high degree of efficiency. Further, a radial ultrasound tomographic image of a desired scanning area can be obtained accurately.

Further, a starting scanning point B and a finishing scanning point c are set on the target-subject image 2, and by setting the area of the body cavity 1 corresponding to these two specified points, A and B, as a scanning area, because a linear ultrasound tomographic image 5', of the scanning area 3 is obtained by scanning said scanning area 3 with the ultrasonic wave S1, the trouble of having to manually direct the ultrasonic wave S1 onto a desired scanning area is eliminated, whereby an ultrasound tomographic image can be obtained expediently and a linear ultrasound tomographic image of a desired scanning area can be obtained with a high degree of efficiency. Further, a linear ultrasound tomographic image of a desired scanning area can be obtained accurately.

Still further, if the target-subject image 2 and the radial ultrasound tomographic image 4' or the linear ultrasound tomographic image 5' are displayed concurrently, an operator can observe the target-subject image 2 and the radial ultrasound tomographic image 4' or the linear ultrasound tomographic image 5' concurrently, whereby the overall convenience attained in the practical application of the endoscope apparatus is improved.

In addition, because a 20 MHz ultrasonic wave, which is capable of reaching deep portions of a human body and exhibits good reflectivity characteristics with respect to a living-tissue subject, has been used as the signal wave, an ultrasound tomographic image including deep portions of a human body can be obtained.

Further, as variations of the current embodiment: an endoscope apparatus wherein by performing scanning according to the same scanning methodology employed in the second embodiment, a 3-dimensional radial ultrasound tomographic image of the section of the body cavity between two points that have been specified on the target-subject image 2, or a 3-dimensional linear ultrasound tomographic image of an area enclosed by four points that have been specified on the target-subject image 2 can be obtained and displayed; or in the reverse, an endoscope apparatus wherein the point on the target-subject image 2 corresponding to a 3-dimensional point that has been specified on a 3-dimensional radial ultrasound tomographic image or a 3-dimensional linear ultrasound tomographic image is displayed; whereby the same effects as were obtained in the second embodiment can be obtained.

What is claimed is:

1. An endoscope apparatus comprising:
   a target-subject image obtaining means for projecting an illuminating-light onto a target subject, obtaining an image formed of a reflected-light reflected from the target subject upon the irradiation thereof with the illuminating-light, and forming a target subject image based on said obtained image formed of said reflected-light,
   a target-subject image display means for displaying a target-subject image formed by said target-subject image obtaining means, and
   a tomographic image obtaining means for scanning a scanning area within the target subject with a signal-wave and obtaining a tomographic image of the scanned area, further comprising
      a position specifying means for specifying one or more desired points on a target-subject image displayed on the target-subject image display means, and
      a scanning-area setting portion for setting a scanning area to be scanned with the signal-wave, based on the point(s) specified by the position specifying means.

2. An endoscope apparatus as defined in claim 1, further comprising
   a tomographic image display means for displaying a tomographic image obtained by the tomographic image obtaining means, wherein
      said tomographic image display means concurrently displays the target-subject image and the tomographic image.

3. An endoscope apparatus as defined in claim 2, wherein
   the position specifying means is a means for specifying three or more desired points,
   the scanning area setting means sets as the scanning area an area on the target subject enclosed by the points thereon corresponding to the three or more points specified by the position specifying means,
   the tomographic image obtaining means is a means for obtaining a plurality of linear tomographic images, further comprising a 3-dimensional tomographic image forming means for forming a 3-dimensional linear tomographic image based on a plurality of radial tomographic images obtained by the tomographic image obtaining means.

4. An endoscope apparatus as defined in claim 3, wherein when a 3-dimensional tomographic image is to be obtained, the endoscope apparatus further comprises
   a memory means for recording a pixel position on the target-subject image and the relation between said pixel position and a pixel position on a 3-dimensional tomographic image,
   a 3-dimensional position specifying means for specifying a desired point on the 3-dimensional tomographic image displayed on the tomographic image display means, and
   a 3-dimensional specified point display means for reading out from the memory means the pixel positions of the point specified by the 3-dimensional position specifying means and the point on the target-subject image corresponding thereto, and displaying the 3-dimensional point and the point corresponding thereto on the target-subject image.

5. An endoscope apparatus as defined in claim 1, wherein
   the position specifying means is a means for specifying two desired points,
   the scanning-area setting means sets as the scanning area an area on the target subject including the points thereon corresponding to the two points specified by the position specifying means, and
   the tomographic image obtaining means is a means for obtaining a plurality of radial tomographic images, further comprising
      a 3-dimensional tomographic image forming means for forming a 3-dimensional radial tomographic image based on a plurality of radial tomographic images obtained by the tomographic image obtaining means.

6. An endoscope apparatus as defined in claim 2, wherein
   the position specifying means is a means for specifying two desired points,
   the scanning-area setting means sets as the scanning area an area on the target subject including the points thereon corresponding to the two points specified by the position specifying means, and
   the tomographic image obtaining means is a means for obtaining a plurality of radial tomographic images, further comprising
      a 3-dimensional tomographic image forming means for forming a 3-dimensional radial tomographic image based on a plurality of radial tomographic images obtained by the tomographic image obtaining means.

7. An endoscope apparatus as defined in claim 6, wherein when a 3-dimensional tomographic image is to be obtained, the endoscope apparatus further comprises
   a memory means for recording a pixel position on the target-subject image and the relation between said pixel position and a pixel position on a 3-dimensional tomographic image,
   a 3-dimensional position specifying means for specifying a desired point on the 3-dimensional tomographic image displayed on the tomographic image display means, and
   a 3-dimensional specified point display means for reading out from the memory means the pixel positions of the point specified by the 3-dimensional position specifying means and the point on the target-subject image corresponding thereto, and displaying the 3-dimensional point and the point corresponding thereto on the target-subject image.

8. An endoscope apparatus as defined in claim 5, wherein when a 3-dimensional tomographic image is to be obtained, the endoscope apparatus further comprises
   a memory means for recording a pixel position on the target-subject image and the relation between said pixel position and a pixel position on a 3-dimensional tomographic image,
   a 3-dimensional position specifying means for specifying a desired point on the 3-dimensional tomographic image displayed on the tomographic image display means, and
   a 3-dimensional specified point display means for reading out from the memory means the pixel positions of the point specified by the 3-dimensional position specifying means and the point on the target-subject image corresponding thereto, and displaying the 3-dimensional point and the point corresponding thereto on the target-subject image.

9. An endoscope apparatus as defined in claim 1, wherein
   the position specifying means is a means for specifying three or more desired points,
   the scanning area setting means sets as the scanning area an area on the target subject enclosed by the points thereon corresponding to the three or more points specified by the position specifying means, the tomographic image obtaining means is a means for obtaining a plurality of linear tomographic images, further comprising a 3-dimensional tomographic image forming means for forming a 3-dimensional linear tomographic image based on a plurality of radial tomographic images obtained by the tomographic image obtaining means.

10. An endoscope apparatus as defined in claim 9, wherein when a 3-dimensional tomographic image is to be obtained, the endoscope apparatus further comprises a memory means for recording a pixel position on the target-subject image and the relation between said pixel position and a pixel position on a 3-dimensional tomographic image, a 3-dimensional position specifying means for specifying a desired point on the 3-dimensional tomographic image displayed on the tomographic image display means, and a 3-dimensional specified point display means for reading out from the memory means the pixel positions of the point specified by the 3-dimensional position specifying means and the point on the target-subject image corresponding thereto, and displaying the 3-dimensional point and the point corresponding thereto on the target-subject image.

11. An endoscope apparatus as defined in any one of claims 1 through 4, wherein the aforementioned signal-wave is a low-coherence light, and the tomographic image obtaining means is an optical tomographic image obtaining means, which scans the scanning area with the low-coherence light and utilizes the reflected-light reflected from a predetermined depth of the scanning area and a reference-light having a slight difference in frequency with respect to the signal-light, for obtaining an optical tomographic image of the scanning area.

12. An endoscope apparatus as defined in claim 11, wherein the target subject is a living-tissue subject, and the wavelength of the low-coherence light is within the 600–1700 nm wavelength range.

13. An endoscope apparatus as defined in any one of claims 1 through 4, wherein the aforementioned signal-wave is an ultrasonic wave, and the tomographic image obtaining means is an ultrasonic tomographic image obtaining means, which scans the scanning area with the ultrasonic wave and utilizes the reflected-wave reflected from a predetermined depth of the scanning area, for obtaining an ultrasound tomographic image of the scanning area.

14. An endoscope apparatus as defined in claim 13, wherein the target subject is a living-tissue subject, and the frequency of the ultrasonic wave is between 1 MHz and 50 MHz.

15. An endoscope apparatus as defined in claim 1, further comprising:

a scanning control portion which guides the target-subject image obtaining means, wherein the illuminating-light projecting from said target-subject image obtaining means is directed to a point on the target subject, and wherein the scanning control portion guides the target-subject image obtaining means so as to position the point on the target subject to be coincident with the one or more desired points on the target subject image display means.

* * * * *